United States Patent
Thorne

[11] Patent Number: 5,980,488
[45] Date of Patent: Nov. 9, 1999

[54] MEDICAL NEEDLE SAFETY APPARATUS AND METHODS

[75] Inventor: David L. Thorne, Kaysville, Utah

[73] Assignee: Specialized Health Products, Inc., Bountiful, Utah

[21] Appl. No.: 09/118,624

[22] Filed: Jul. 17, 1998

Related U.S. Application Data

[63] Continuation of application No. 08/927,053, Sep. 10, 1997, Pat. No. 5,823,997, which is a continuation-in-part of application No. 08/744,108, Nov. 5, 1996, Pat. No. 5,763,974, which is a continuation of application No. 08/595,802, Feb. 2, 1996, Pat. No. 5,656,031, which is a continuation of application No. 08/565,881, Dec. 1, 1995, Pat. No. 5,616,135, which is a continuation of application No. 08/455,514, May 31, 1995, Pat. No. 5,549,708, which is a continuation of application No. 08/370,728, Jan. 10, 1995, Pat. No. 5,480,385, and a continuation of application No. 08/436,976, May 8, 1995, Pat. No. 5,487,734, and a continuation of application No. 08/484,533, Jun. 7, 1995, Pat. No. 5,542,927, which is a continuation-in-part of application No. 08/436,976, and application No. 08/484,533, which is a continuation-in-part of application No. 08/370,728.

[51] Int. Cl.⁶ ............................................... A61M 5/00
[52] U.S. Cl. ........................... 604/110; 604/192; 604/263
[58] Field of Search ................................. 604/110, 187, 604/192, 198, 263

[56] References Cited

U.S. PATENT DOCUMENTS

| | | | |
|---|---|---|---|
| 5,139,489 | 8/1992 | Hollister | 604/192 |
| 5,147,303 | 9/1992 | Martin | 604/110 |
| 5,154,285 | 10/1992 | Hollister | 206/365 |
| 5,193,552 | 3/1993 | Columbus et al. | 128/760 |
| 5,246,428 | 9/1993 | Falknor | 604/198 |
| 5,254,099 | 10/1993 | Kuracina et al. | 604/198 |
| 5,256,153 | 10/1993 | Hake | 604/198 |
| 5,356,392 | 10/1994 | Firth et al. | 604/198 |
| 5,403,283 | 4/1995 | Luther | 604/164 |
| 5,480,385 | 1/1996 | Thorne et al. | 604/110 |
| 5,487,734 | 1/1996 | Thorne et al. | 604/195 |
| 5,542,927 | 8/1996 | Thorne et al. | 604/110 |
| 5,549,708 | 8/1996 | Thorne et al. | 604/110 |
| 5,573,510 | 11/1996 | Isaacson | 604/158 |

*Primary Examiner*—John D. Yasko
*Attorney, Agent, or Firm*—Gale H. Thorne

[57] ABSTRACT

Parts which may be integrally molded with a phlebotomy barrel or with a Luer fitting to provide, in a single molded part, an extendable safety enclosure for a medical cannula in phlebotomy, syringe and other general medical needle applications. Integrally molded part phlebotomy safety devices are disclosed which require only the integrally-molded part, a medical needle, a label and a transport needle cover to form a ready-to-use phlebotomy device. Upon removal of the label and needle cover, the device is ready for use in a medical procedure. The enclosure comprises a plurality of rigid segments serially connected by a plurality of intersegment hinges, which are preferably living hinges. The segments are disposed about a medical needle, folded upon each other during the medical procedure and extended at the end of the procedure to form a secure, substantially rigid safety shroud. During the procedure, the enclosure is folded and conveniently disposed about a proximal portion of the needle. At the end of the procedure, the enclosure is extended to protectively sheath and secure the needle in a substantially rigid structure formed in combination by the enclosure and the needle.

13 Claims, 14 Drawing Sheets

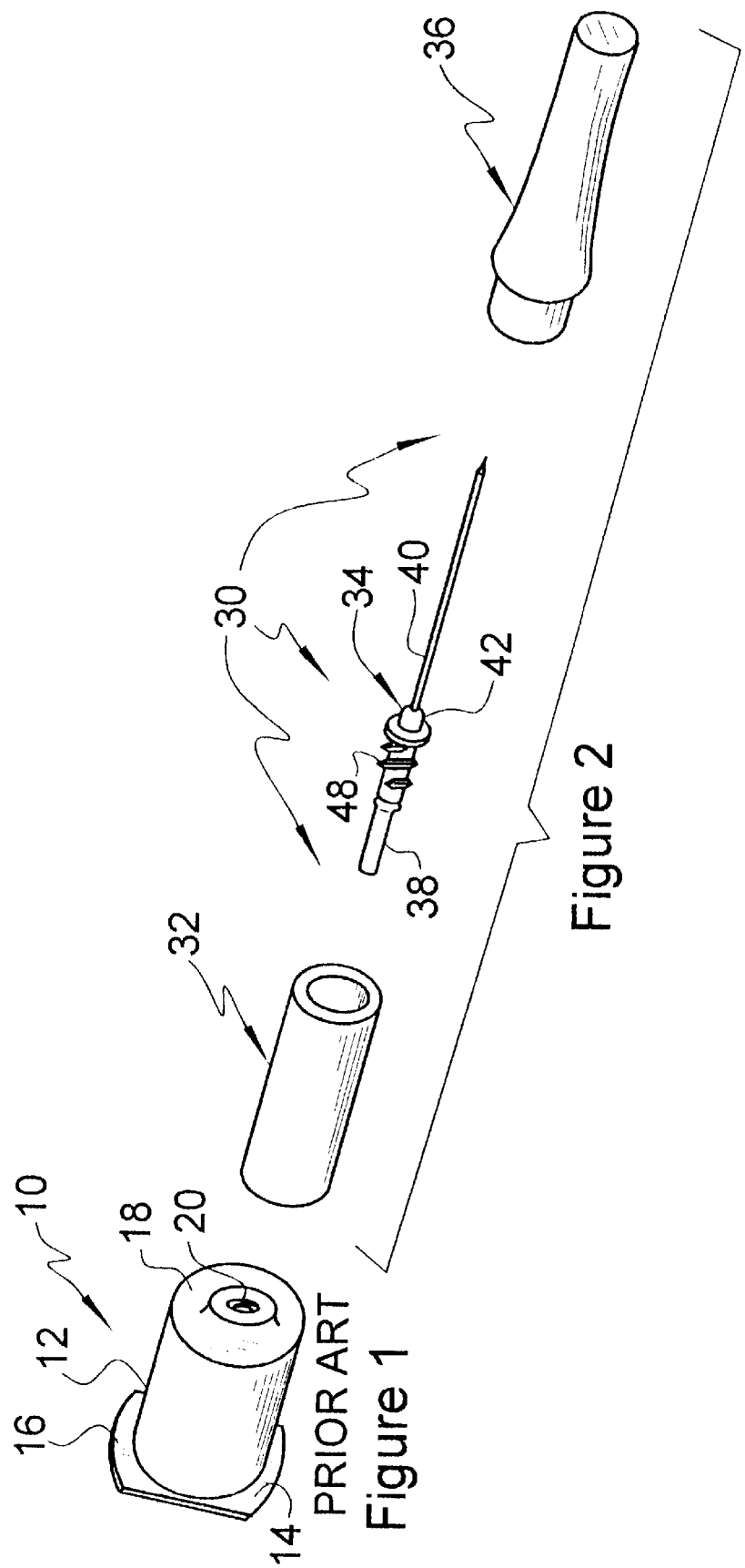

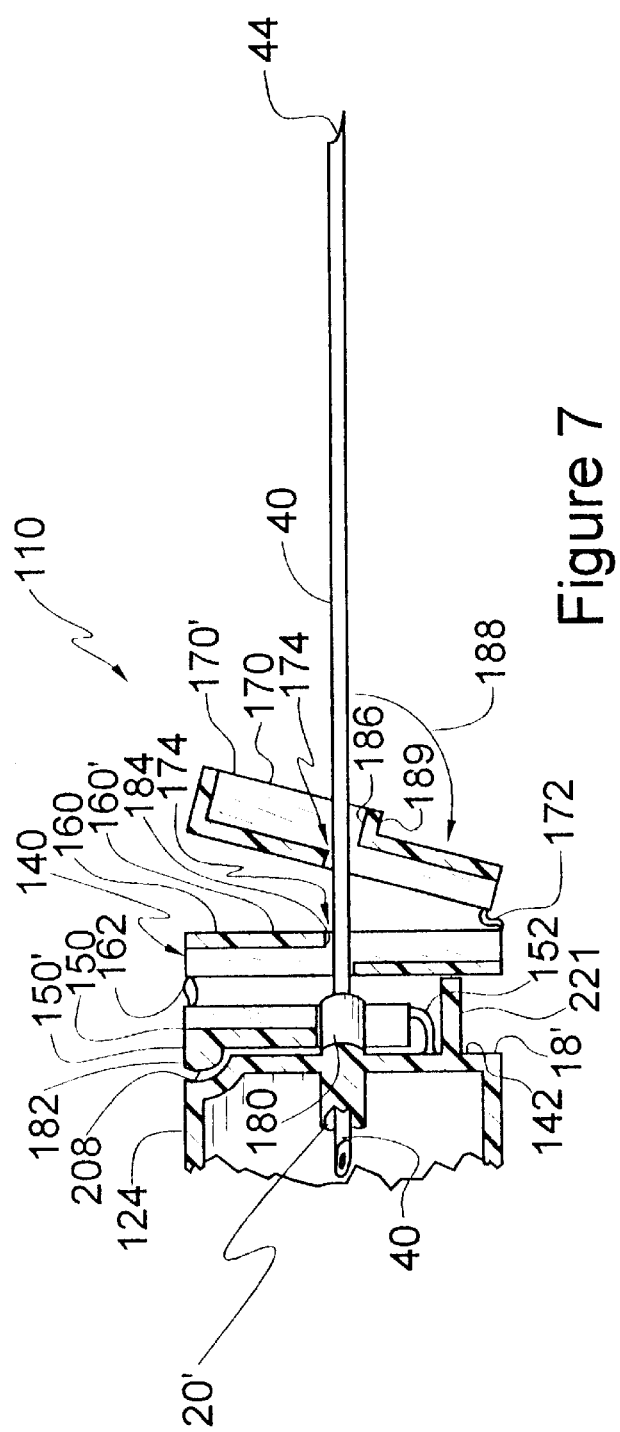
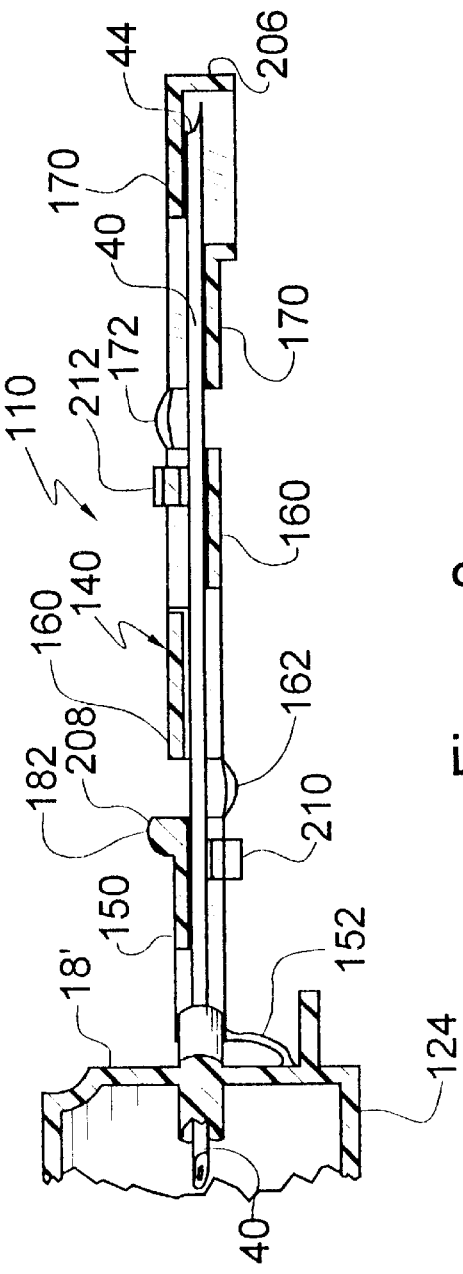
Figure 7
Figure 8

MEDICAL NEEDLE SAFETY APPARATUS AND METHODS

This application for patent is a continuation of application Ser. No. 08/927,053, filed Sep. 10, 1997, now U.S. Pat. No. 5,823,997 which is a continuation-in-part of U.S. patent application Ser. No. 08/744,108 filed Nov. 5, 1996 now U.S. Pat. No. 5,763,974 entitled Self Retracting Medical Needle Apparatus and Methods, which is a continuation of U.S. patent application Ser. No. 08/595,802 filed Feb. 2, 1996 now U.S. Pat. No. 5,656,031 entitled Medical Syringe and Self Retracting Needle Apparatus, which is a continuation of U.S. patent application Ser. No. 08/565,881 filed, Dec. 1, 1995, now U.S. Pat. No. 5,616,135 issued Apr. 1, 1997 entitled Self Retracting Medical Needle Apparatus and Methods, which is a continuation of U.S. patent application Ser. No. 08/455,514 filed May 31 1995, now U.S. Pat. No. 5,549,708 issued Aug. 27, 1996 entitled Self Retracting Medical Needle Apparatus and Methods, which is a continuation of U.S. patent application Ser. No. 08/370,728 filed Jan. 10, 1995, now U.S. Pat. No. 5,480,385 issued Jan. 2, 1996 entitled Self Retracting Catheter Needle Apparatus and Methods, U.S. patent application Ser. No. 08/436,976 filed May 8, 1995, now U.S. Pat. No. 5,487,734 issued Jan. 30, 1996 entitled Self Retracting Catheter Needle Apparatus and Methods, U.S. patent application Ser. No. 08/434,533 filed Jun. 7, 1995, now U.S. Pat. No. 5,542,927 issued Aug. 6, 1996 entitled Self Retracting Syringe Needle Apparatus and Methods, each is a continuation-in-part of Ser. No. 08/370,728 filed Jan. 10, 1995, now U.S. Pat. No. 5,480,385, all disclosures of which are specifically incorporated herein by reference.

FIELD OF INVENTION

This invention relates generally to safety devices for hollow bore medical needles and particularly to medical phlebotomy, syringe, butterfly and other hollow needle products which comprise protective needle sheaths for securely shielding sharp medical needle tips after being withdrawn from a patient. This invention more particularly relates to sheaths or shrouds which are extended to a locked, needle-covering position after the needle is withdrawn from the patient.

PRIOR ART

Problems associated with inadvertent needle sticks are well known in the art of blood sampling, percutaneous medication injection and other medical procedures involving uses of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices).

Examples of disclosures of safety devices which protect needles by moving a protective shield over a sharp end of a syringe or other hollow bore medical needle are found in U.S. Pat. No. 5,348,544, issued Sep. 20, 1994 to Sweeney et al. (Sweeney), U.S. Pat. No. 5,246,428 issued Sep. 21, 1993 to Donald W. Falkor (Falkor), U.S. Pat. No. 5,256,153 issued Oct. 26, 1993 to Lawrence W. Hake (Hake) and U.S. Pat. Nos. 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

Sweeney discloses a device comprising a guard which is manually, slidably movable along a needle canula from a position proximal to a user to a distal position where the needle tip is shielded. The device comprises a hinged arm which extends along the needle canula and which is moved distally to collapse upon itself to extend the shield over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the guard. Once the device is extended to shield a needle tip, it cannot be easily reset to recover use of the needle for a subsequent procedure. Also, the hinged arm requires activation in the region of the needle itself and comprises parts which are of a size which occasionally impedes a user's line of sight to insertion locations.

Fallmer, and related disclosures, disclose devices comprising shields which are automatically releasable to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make reading portions of volume measurement indicia on the syringe body difficult to read with accuracy when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle stick.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible out of the way during a medical procedure. Such a format requires five injection molded parts, including a disposable needle assembly.

Generally, other than acceptance of the type of operation offered by such devices, commercial viability is dependent upon manufacturig cost. Purchase decisions in the area in which these devices are used are very cost sensitive. If gains in either improvement in safety or in labor savings are not found to make a device sufficiently competitive with contemporary competitive items, those devices are usually not found to be commercially viable. In U.S. Pat. No. 5,480,385, from which this patent filing continues, a medical needle safety phlebotomy apparatus disclosing an integrally constructed barrel and medical needle assembly fabricated and used as a single disposable unit is disclosed. By making the apparatus unitary including both barrel and needle, only four injection molded parts is required. Four injection molded parts in a needle retraction safety device is emphasized therein as a significant factor in cost reduction. Motivation for providing a cost competitive self-retracting needle apparatus coupled with improved safety of use of the apparatus are the basis for conception of the instant inventions disclosed herein.

BRIEF SUMMARY AND OBJECTS OF THE INVENTION

In brief summary, the novel inventions disclosed herein dramatically diminish known major problems resulting from injury-related needle sticks which occur when needle tips are bared as medical needles are withdrawn from a patient at the end of a needle insertion procedure, but, perhaps more important to general patient welfare, these inventions provide opportunity for fabrication of a very low cost safety needle system. Low cost is achieved by a dramatic reduction in injection molded parts wherein a needle covering safety sheath is integrally molded with other parts such as a hub of the needle or a barrel segment of an integral phlebotomy device.

In current standard non-safety phlebotomy devices, each needle assembly generally comprises a cannula having two sharpened ends to form a medical needle, a needle hub, a blood valve sheath (commonly called a snubber), two covers for protecting both sharp ends and a paper seal to tape the two covers together and form an environmental protective barrier for the needle prior to use. Thus, with the barrel, six parts (including four injection molded parts) are currently used in contemporary, non-safety systems. In the phlebotomy application, employment of the instant inventions disclosed and claimed herein produces a safety phlebotomy device requiring only two injection molded parts, and only five parts overall. This number of parts compares well with the number of parts required in barrel and needle assemblies which make up the contemporary non-safety systems and is much better when compared against other safety phlebotomy systems.

Generally, basis for the invention is a foldable needle sheath which folds about a medical needle to permit access to the needle in a medical procedure. The sheath is hingeably attached to structure (e.g. a needle hub or phlebotomy barrel) at a point away from a sharpened needle tip which is later enclosed to protect a user. At the end of the procedure, the sheath is unfolded and extended away from the structure in the direction of the needle tip to encase and thereby protect users from contact with the needle and its tip. To permit the sheath to unfold about the needle, each folded part of the sheath is serially constructed of a plurality of rigid segments. Each segment comprises an orifice through which the needle passes and about which the segments rotate while the sheath is being extended. Each segment is connected to at least one other segment by a hinge, which is preferably a molded living hinge, and comprises a channel into which the needle nests when the sheath is fully extended. At least one of the segments comprises a catch which securely captures the needle when it is disposed in the sheath. Once the sheath is extended and the needle so captured, the combination of sheath and needle form a substantially rigid member which shrouds the needle and its sharpened tip to provide safety from dangerous contact with the tip and needle. All hingeable attachments are preferably living hinges integrally and concurrently formed with other sheath parts.

Accordingly, it is a primary object to provide a manually actuated safety sheath for a medical needle which is a single molded part.

It is another object to provide a safety sheath which is integrally molded with another part of a medical needle device (e.g. with a phlebotomy barrel or a medical needle hub).

It is a particularly important object to provide a sheath which is fold out-of-the-way in one state whereby a medical needle may be used in a medical procedure and which unfolded to combine with the medical needle to form a substantially rigid needle shrouding structure which protects against inadvertent contact with a sharpened tip of the needle.

It is also an important object to provide a shroud which averts contact with the needle along the length of the needle when the shroud is displaced to protect the needle and its tip.

It is an important object to provide an integral, self-contained, safety phlebotomy system comprising a barrel and needle assembly and a safety shroud, the entire system requiring but two injection molded parts.

It is another important object to provide an integral, self-contained safety phlebotomy system which only requires five parts, including a needle cover, a barrel, an adhesive label, a medical needle and needle hub.

These and other objects and features of the present invention will be apparent from the detailed description taken with reference to accompanying drawings.

BRIEF DESCRIPTION OF THE DRAWINGS

FIG. 1 is a perspective of a barrel part which is in current use in blood sampling or phlebotomy.

FIG. 2 is an exploded perspective of parts which make up a needle system which is in current use in blood sampling or phlebotomy, the needle system is in use in combination with the barrel part of FIG. 1.

FIG. 7 is a section, taken along lines 7—7 of FIG. 6, illustrating a forepart which includes a safety sheath disposed about a medical needle.

FIG. 8 is a section of the part seen in FIG. 7 disposed for needle containment.

DETAILED DESCRIPTION OF THE ILLUSTRATED EMBODIMENTS

Figure 3:
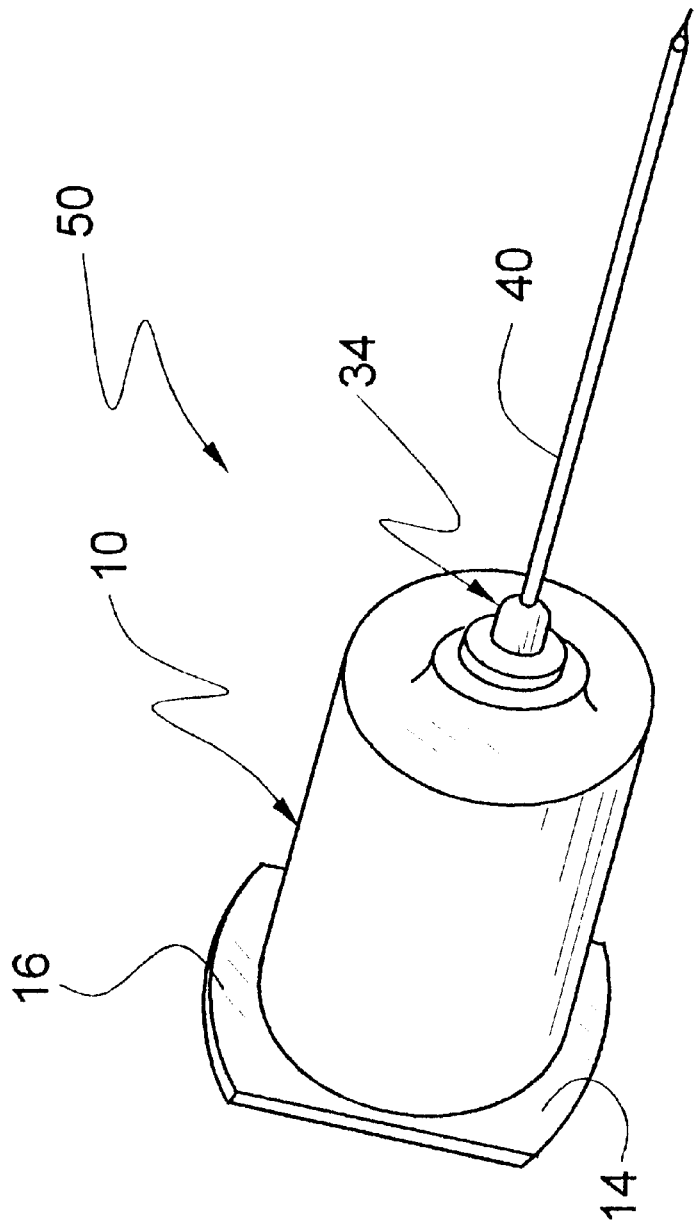
FIG. 3 is a ready-to-use combination of the barrel part, seen in FIG. 1, securely, but releasible affixed to a needle assembly portion of the needle system of FIG. 2, thus prepared for a phlebotomy procedure.

In this description. unless a specific object is referenced, the term proximal is used to indicate the segment of a device normally closest to a user (the clinician or technician who is treating a patient). In like manner, the term distal refers to the other (away from the user) end. Reference is now made to the embodiments illustrated in FIGS. 1–19 wherein like numerals are used to designate like parts throughout. In some cases, parts having similar form and function to parts earlier cited are enumerated with prime numerals of earlier cited parts.

Reference is now made to FIGS. 1–4 wherein parts and assemblies in common current use in blood sampling or phlebotomy procedures are illustrated. A barrel part 10 is seen in FIG. 1. Generally, such barrel parts comprise a substantially hollow cylindrical portion 12 having apair of laterally extending wings 14 and 16 which are disposed about a sample tube receiving orifice (not seen). A substantially closed end 18 opposes the orifice and generally comprises a threaded opening 20.

Figure 4:
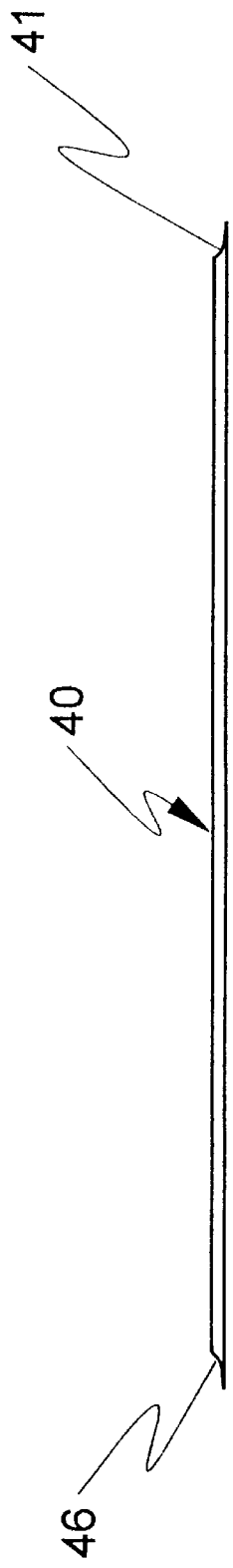
FIG. 4 is a side view of a phlebotomy needle.

An exploded view of a transport needle assembly 30 is seen in FIG. 2. Assembly 30 generally comprises a back cover 32, a needle assembly 34 and a front cover 36. Needle assembly 34 comprises a posterior needle valve 38, a double ended needle 40, a needle hub 42. The form of needle 40 is best seen in FIG. 4 wherein needle 40 is seen to comprise a very sharp needle point or tip 44 and a non-coring needle tip 46. Needle tip 44 is formed for efficient percutaneous entry into a patient's vein while tip 46 is formed to repeatedly pierce a pliable stopper on an evacuated sample tube without exacting a core from the stopper.

As part of a contemporary standard procedure, back cover 32 is removed from an unused transport assembly 30 to expose needle valve 38 and a threaded portion 48 of hub 42. Handling the remainder of assembly 30 by front cover 36, portion 48 is inserted into opening 20 and secured by rotation thereto. Cover 36 is then removed to provide a procedure-ready blood sampling device 50, as seen in FIG. 3. Once a blood sampling procedure has been completed, needle assembly 34 must be either removed from barrel 10 and placed into a sharps container or the entire device 50 must be carefully discarded as a unit to assure an inadvertent stick by a contaminated needle does not occur.

It is widely known that often painful and sometimes tragic needle sticks have occurred before appropriate disposition of a contaminated needle has been accomplished. All to often, care requirements dictate immediate attention being paid to a patient's needs before taking appropriate action relative to discarding a contaminated needle. Even though thoughtful standards regarding care and handling of contaminated needles are in place, inadvertent needle sticks occur all too often. In the face of such occurrences, one might ask why safety products have not replaced those currently commonly used. The answer to such a question likely comprises conclusions reached after reviewing a number of factors involved in device selection. Those factors include cost of individual safety products compared to those currently commonly used, whether or not ergonomic factors (such as required changes in procedure, transport and disposal) are acceptable and ease of implementation of safety attributes. The above factors have been carefully considered by the inventor and are an important portion of the basis for the instant invention disclosed and claimed herein.

Figure 5:
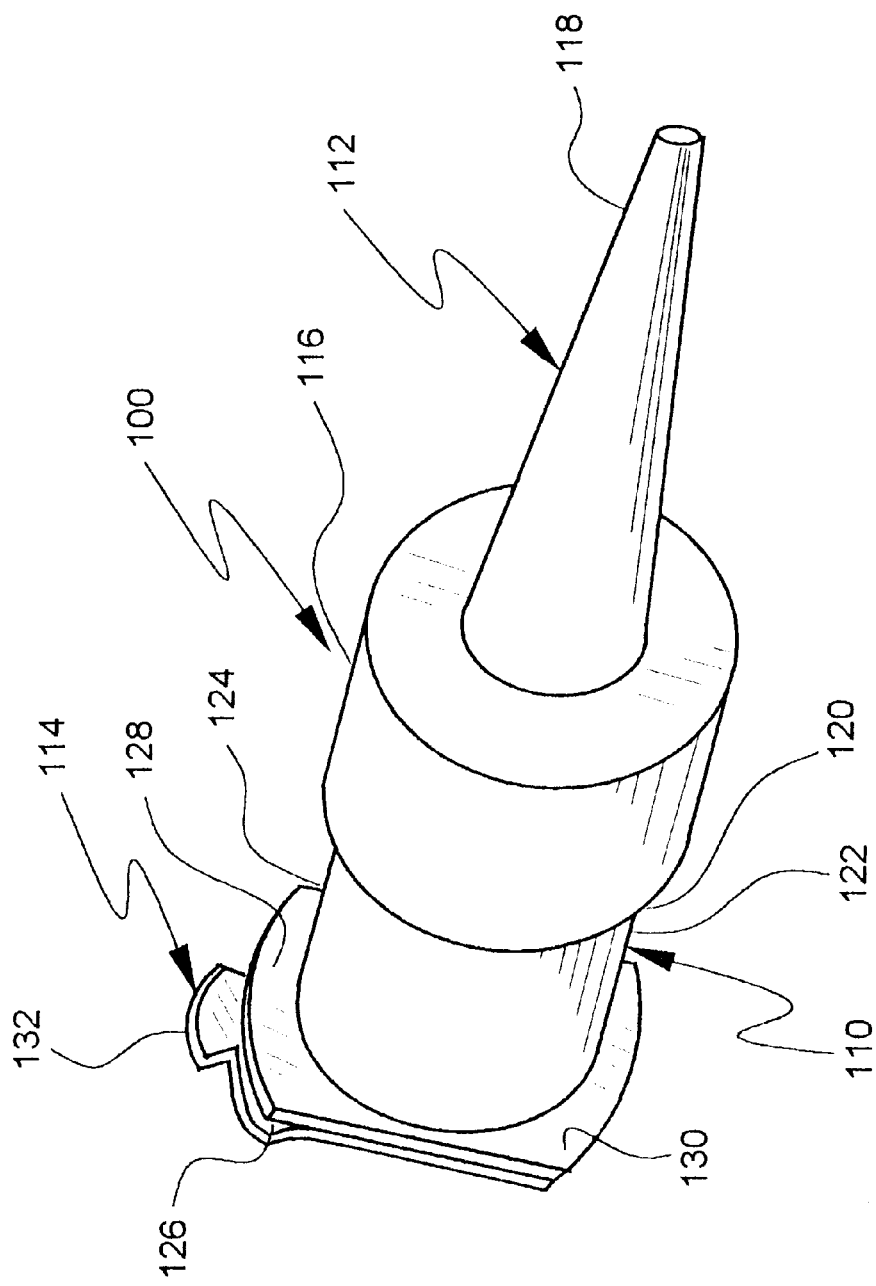
FIG. 5 is a perspective of a pre-use state of one embodiment of the instant invention disclosed herein.

Reference is now made to FIG. 5 wherein one embodiment of the inventions is seen as unitary phlebotomy system 100. System 100 comprises a barrel assembly 110 with a needle 40 (hidden in FIG. 5) securely affixed thereto, a front needle protector 112 and a back seal 114. Barrel assembly 110 and needle 40 make up the primary functional device or unit (generally referenced by 115). Protector 112 and seal 114 are removed prior to commencing a blood sampling procedure.

Generally, protector 112 comprises a proximally disposed, hollow cylindrical portion 116 and a distally disposed needle cover part 118. Portion 116 comprises a section 120 which interfaces with an exterior surface 122 of barrel assembly 10. A sealing label or heat stake (not shown) may be disposed about the area of interface to form a protective seal for those parts of barrel assembly 110 which must be maintained in a sterile and tamper proof environment. Such labels are well known and in wide use in the medical needle and phlebotomy fields.

Barrel assembly 110 comprises a hollow barrel 124 which has a proximally disposed opening 126 for ready insertion of an evacuated blood sampling tube (not shown). As is common today for barrels used for communicating with blood sampling tubes, barrel 124 also comprises a pair of wings 128 and 130 which provide ease of handling when inserting and removing blood sampling tubes from barrel 124.

Figure 6:
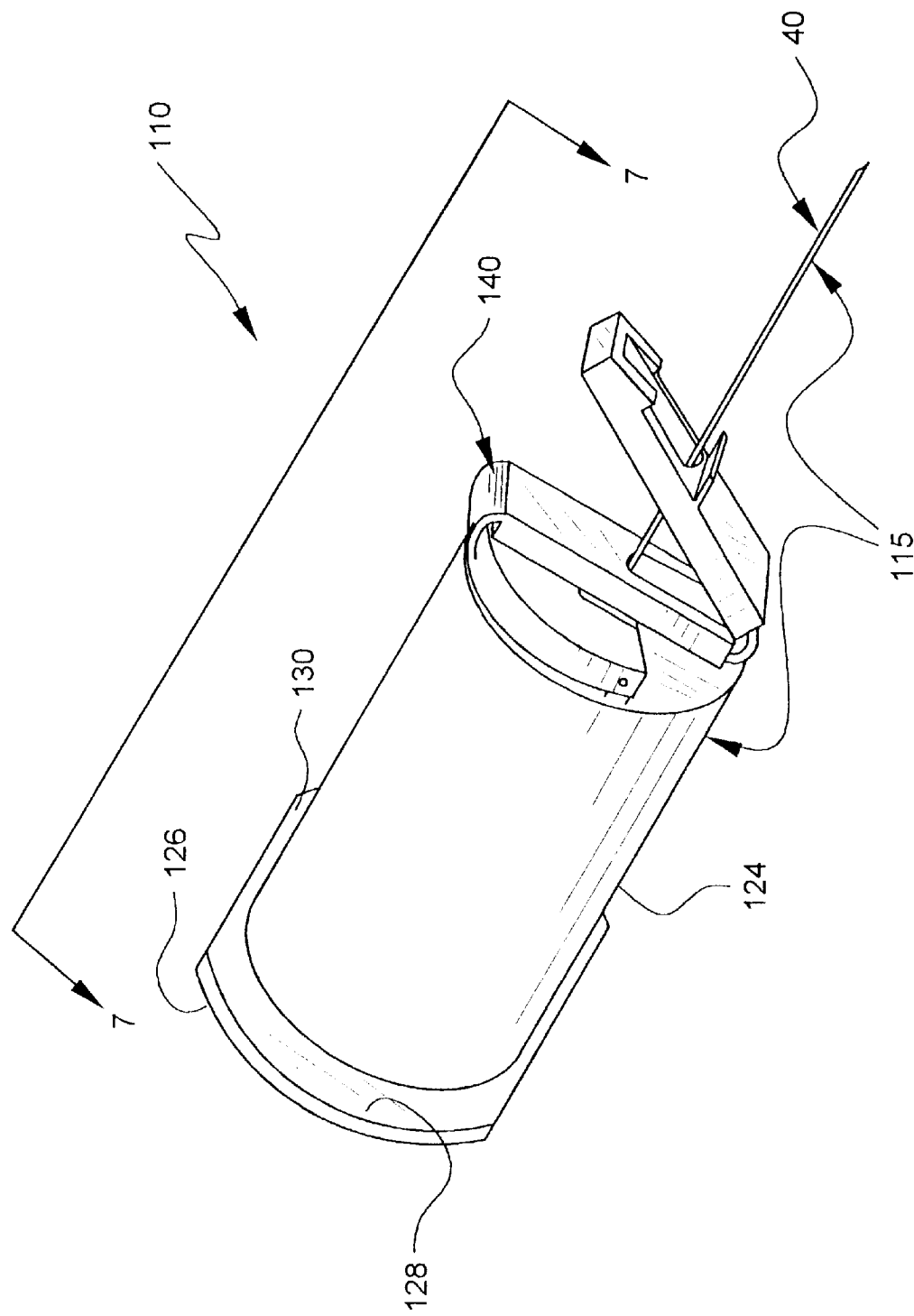
FIG. 6 is a perspective of the embodiment of FIG. 5 with a front cover and a back label removed.

Seal 114 is preferably releasibly, adhesively affixed to barrel assembly 110 over opening 126 and provides a sterile barrier and tamper indicator until removed from barrel assembly 110 for use. Preferably seal 114 comprises a tab 132 which provides for facile removal to seal 114. Seals for similar purposes are well known and widely used in the medical device field. To prepare system 100 for use in a medical procedure, seal 114 and protector 112 are simply removed from barrel assembly 110, as seen in FIG. 6. Note that barrel assembly 110 has been rotated 180° relative to its position in FIG. 5. With cover removed. an extendable needle sheath or shroud 140, generally numbered in other figures as 140', is seen to be disposed about a medical needle 40. Note that, in this embodiment, needle 40 is securely affixed to barrel 124. Attachment of needle 40 to barrel 124 is disclosed in more detail hereafter.

Also in this embodiment, shroud 140 is hingeably affixed to a distal face 142 of barrel 124, preferably through a living hinge such that barrel 124 and shroud 140 are formed as a single molded part. A simplified representation of shroud 140 is seen in FIG. 7. Some parts of shroud 140 have been removed for clarity of presentation of shroud 140 and needle 40 interaction. As seen in FIG. 7, shroud 140 generally comprises a single proximal part, specifically numbered 150, for shroud 140 and 150' for general reference, hinged to barrel 124 via a hinge 152 (preferably a living hinge). It should be noted that, as is disclosed hereafter, shroud 140 may be hingedly affixed to any structurally sound part relative to needle 40, such as a Luer fitting of a syringe, to provide a general medical needle safety shroud or to a phlebotomy barrel.

Generally, a plurality of rigid members are serially hingedly affixed, one to another, to form shroud 140'. In the case of shroud 140, a middle member 160 (generally referenced 160') is hingedly affixed to part 150 (generally referenced by 150') by a hinge 162 (also preferably a living hinge). Also in the case of shroud 140, a distal member 170 (generally referenced 170') is hingedly affixed to part 160 by a hinge 172 (preferably a living hinge, as well). Note that each part 150, 160 and 170 comprises a pathway 174 wherethrough needle 140 passes. Also in FIG. 7, barrel 124 is seen to comprise a centrally disposed hub 180 in a face 18' of barrel 124 through which needle 40 is inserted and securely affixed in an opening 20', making needle 40 a substantially rigid member relative to barrel 124.

Figure 7A:
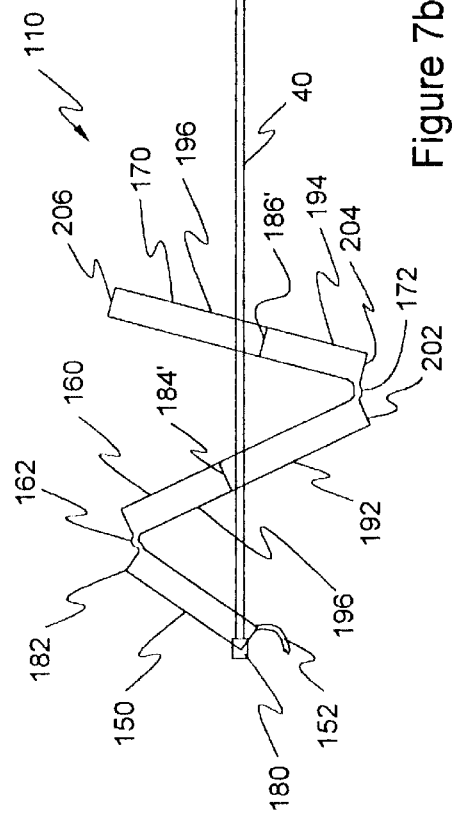
FIGS. 7A–D are schematic representations of the safety sheath seen in FIG. 7 showing relative sheath positions as the sheath is displaced from an operational state to a needle enclosing state.

Reference is now made to FIGS. 7A–D wherein a schematic representation of action of shroud 140 about needle 40 is seen in various steps. Only those primary parts of shroud 140 and needle 40 necessary for understanding movement of shroud 140, relative to needle 40, from an operational state to a needle protecting state are seen in FIGS. 7A–D. As seen in FIG. 7A, part 150 comprises a superior proximal comer 182. Part 160 comprises a ledge member 184 (see FIG. 7), represented by line 184' in FIGS. 7A–D which is disposed to communicate with needle 40 when shroud 140 is caused to move as a result of a distally directed force being applied to proximal comer 182. In similar manner, part 170 comprises a ledge member 186 (see also FIG. 7), represented by line 186' in FIGS. 7A–D which is also disposed to communicate with needle 40 as shroud 140 is moved under application of force to comer 182. Note that rigid part 160 may be divided into a superior part 190 and an inferior part 192, separated by line 184'. Similarly, rigid part 170 may be divided into an inferior part 194 and a superior part 196, separated by line 186'. Further, part 160 comprises a superior face 200 comprising a connection to hinge 162 and an inferior face 202 comprising a connection to hinge 172. Likewise, part 170 comprises an inferior face 204 having a connection to hinge 172 and a superior face 206 which ultimately forms the most distal portion of shroud 140.

Figure 7B:
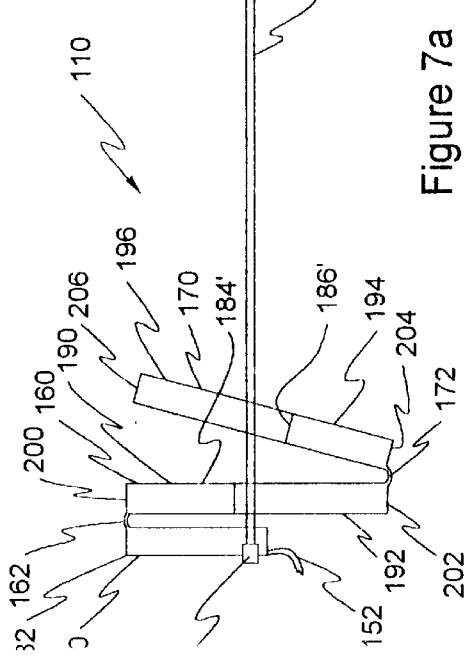
Figure 7C:
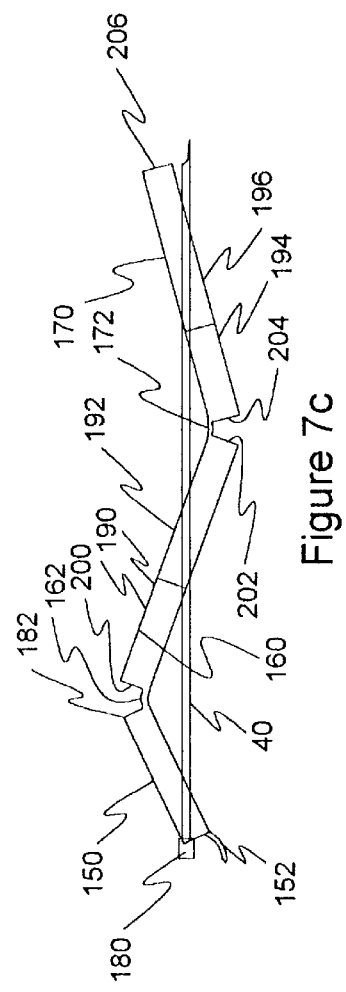
Figure 7D:
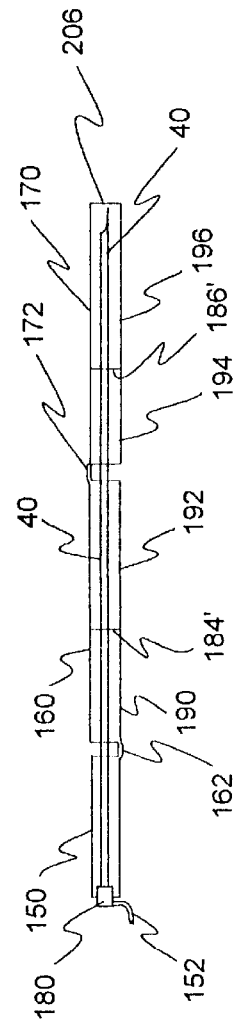

Intermediate dispositions of parts 150, 160 and 170 as continuing distally directed force is applied to comer 182 are seen in FIG. 7B and 7C. Successively, distal application of force causes, in sequence, disposition of parts 150, 160 and 170 of shroud 140 as seen in FIG. 7B and subsequently as seen in FIG. 7C. Note that, as line 184' (ledge member 184) is moved into contact with needle 40, Rotation of part 150 relative to hub 180 is translated into rotation of part 160 through hinge 162. Consequently, part 170 is directed superiorly through hinge 172 until line 186' (ledge member 186) is raised to contact needle 40. Upon contact of line 186' against needle 40, part 170 is rotated in clockwise fashion to extend face 206 to be distally disposed relative to needle tip 44. As seen in FIG. 7D, further rotation of part 150 to a substantially parallel disposition relative to needle 40 results in similar disposition of parts 160 and 170. To assure forces directed upon comer 182 always result in extension of part 170, part 170 should not form an angle (indicated by arc and arrow 188) of equal to or less than 90°. An extended foot 189, seen in FIG. 7, provides extension which functions to provide a linear offset which results in an angular bias to protect against binding when angle 188 is less than 90°. Further, protruding latches 210 and 212, described hereafter, may be used for further bias. A stop 221, seen protruding from face 142 of barrel 124 provides a similar bias, retarding part 160 from binding against needle 40 as corner 182 is displaced distally.

Latching of one or more parts, for example part 150 or 160, to needle 40 causes needle 40 to be enclosed in a substantially rigid safety enclosure. Such an enclosure requires no clip or spring retention as taught by Sweeney. As one who is skilled in mechanical and geometric arts understands, a shroud may be constructed using two or more hinged parts depending upon that needle length and part length required to extend a safety cover about a needle tip.

A partial cross section of barrel assembly 110 with shroud 140 disposed as seen in FIG. 7D is provided in FIG. 8. Note a protuberance 208 superiorly disposed upon part 150 at corner 182 provides a noticeable site upon which to exert a downwardly and distally directed force to cause shroud 140 to extend. Note also, a first latch 210 which catches and securely affixes needle 40 in the safety of recesses of shroud 140. Part 160 comprises a second latch 212 which also catches needle 40 to further assure rigidity of the combination formed by shroud 140 and needle 40. Form of exemplary latches having form and function similar to latches 210 and 212 are disclosed in detail hereafter.

Figure 9:
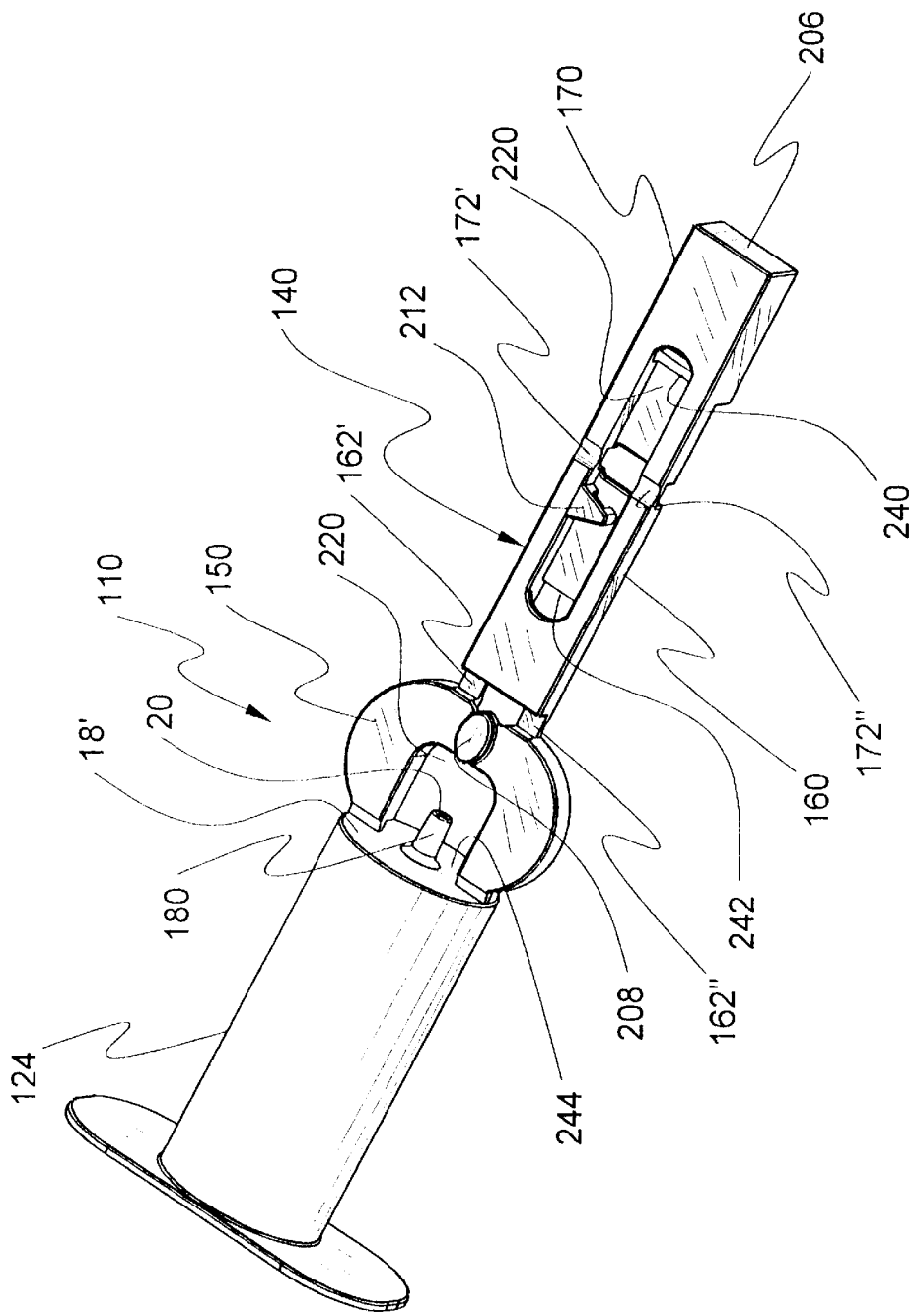
FIG. 9 is a superior perspective of an as-molded part of a barrel portion of the embodiment seen in FIG. 5.
Figure 10:
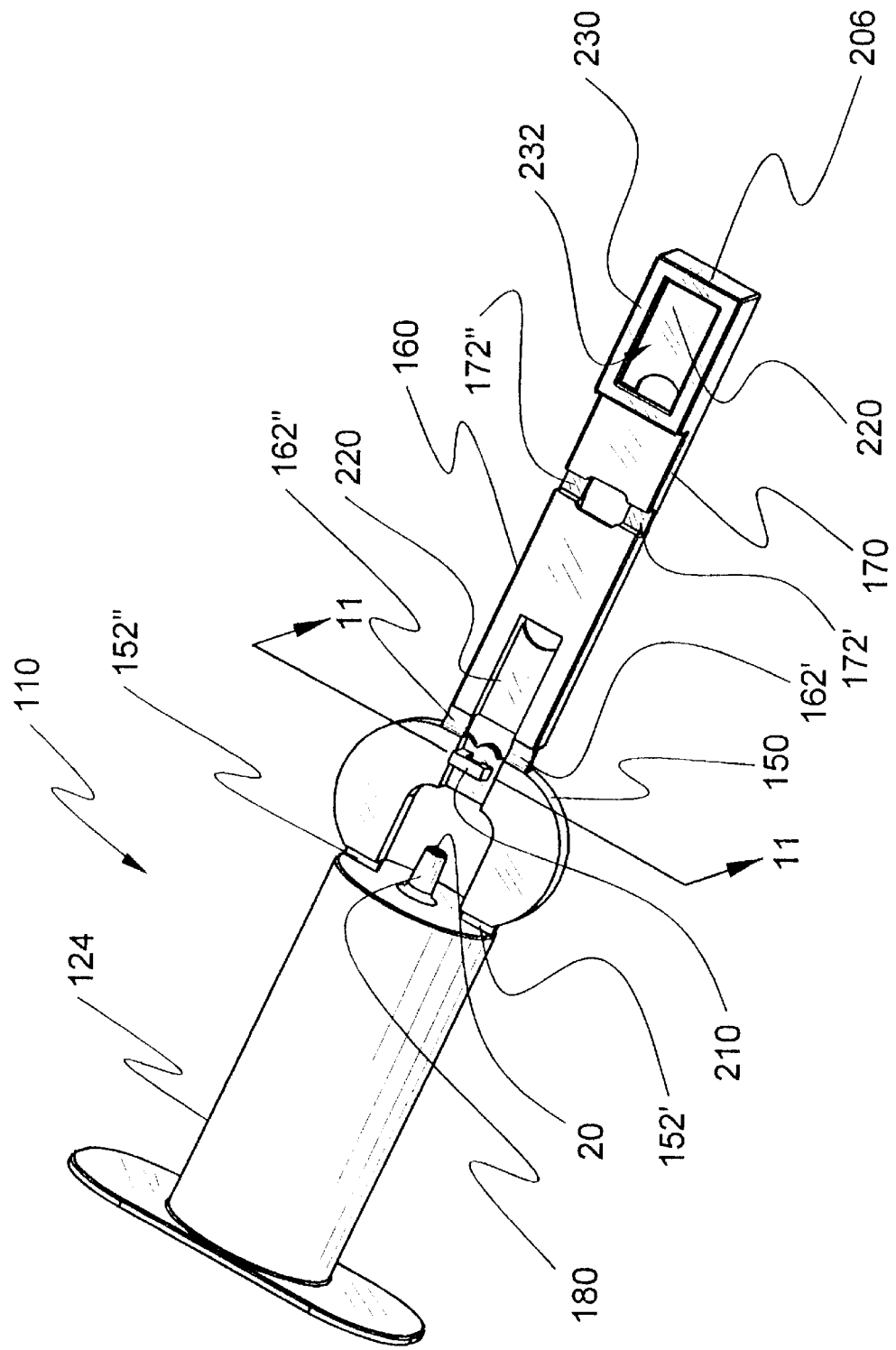
FIG. 10 is an inferior perspective of the part seen in FIG. 9.

FIGS. 9 and 10 show superior and inferior perspectives, respectively, of barrel assembly 110 before needle attachment. Barrel assembly 110 in FIGS. 9 and 10 are in an "as-molded" state. Barrel assembly is preferably injection molded in such a state using polypropylene synthetic resinous material, although other material which supports both fabrication living hinges and which has sufficient material characteristics to perform adequately as a hub for needle 40 and a phlebotomy barrel may be used.

Note that parts 150, 160 and 170, when aligned in a common plane, comprise a common channel or pathway 220 for needle 40. Hinges previously referenced as 162 and 172 are each seen to be double hinge pairs, 162' and 162" and 172' and 172", respectively. The double hinge pairs are disposed on each side of pathway 220 to permit folding and unfolding of shroud 140 without interfering with needle 40. Hinge 152 is similarly comprised of a hinge pair 152' and 152". As best seen in FIG. 10, part 170 comprises a raised section 230. Forming a deep well 232 for tip 44 when needle 40 is extended to provide further protection against inadvertent access to needle tip 44 when shroud 140 is elongated to its needle safety state.

As seen in FIGS. 9 and 10, hub 180 is disposed in line with pathway 220. Attention is now drawn to FIG. 9 wherein part 170 is seen to comprise a centrally disposed orifice 240. Part 160 is seen to comprise a similarly disposed orifice 242. In combination a barrel face 18' of barrel 124 and part 150, form an opening 244 about hub 180. To form a usable assembly, shroud 140 is folded as seen in FIG. 6 and needle 40 is inserted through orifices 240 and 242 and opening 244 (along pathway 174) into hub 180 and securely affixed thereto. Affixing of needles within hubs is well known to those skilled in manufacturing processes in hollow medical needle device assembly. Note that insertion of needle 40 through orifices 240, 242 and opening 244 involves needle 40 as an active member in the process of extending shroud 140.

Figure 11:
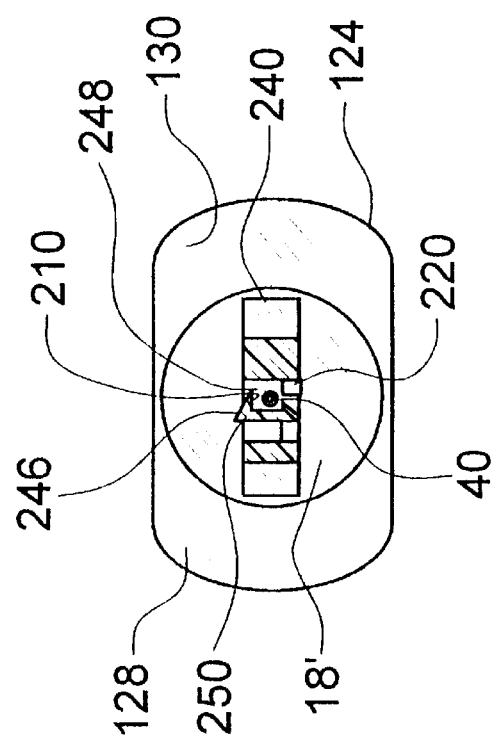
FIG. 11 is a section taken along lines 11—11 in FIG. 10.

Reference is now made to FIG. 11 wherein latch 210 is seen in cross section. Latch 210 is displaceable when it comes in contact with needle 40. For this purpose, latch 210 preferably comprises an inclined outward surface 246 slanting toward an opening 248 which elastically accommodates entry and final disposition below latch head 250. Latch 212 is similarly formed.

Figure 12:
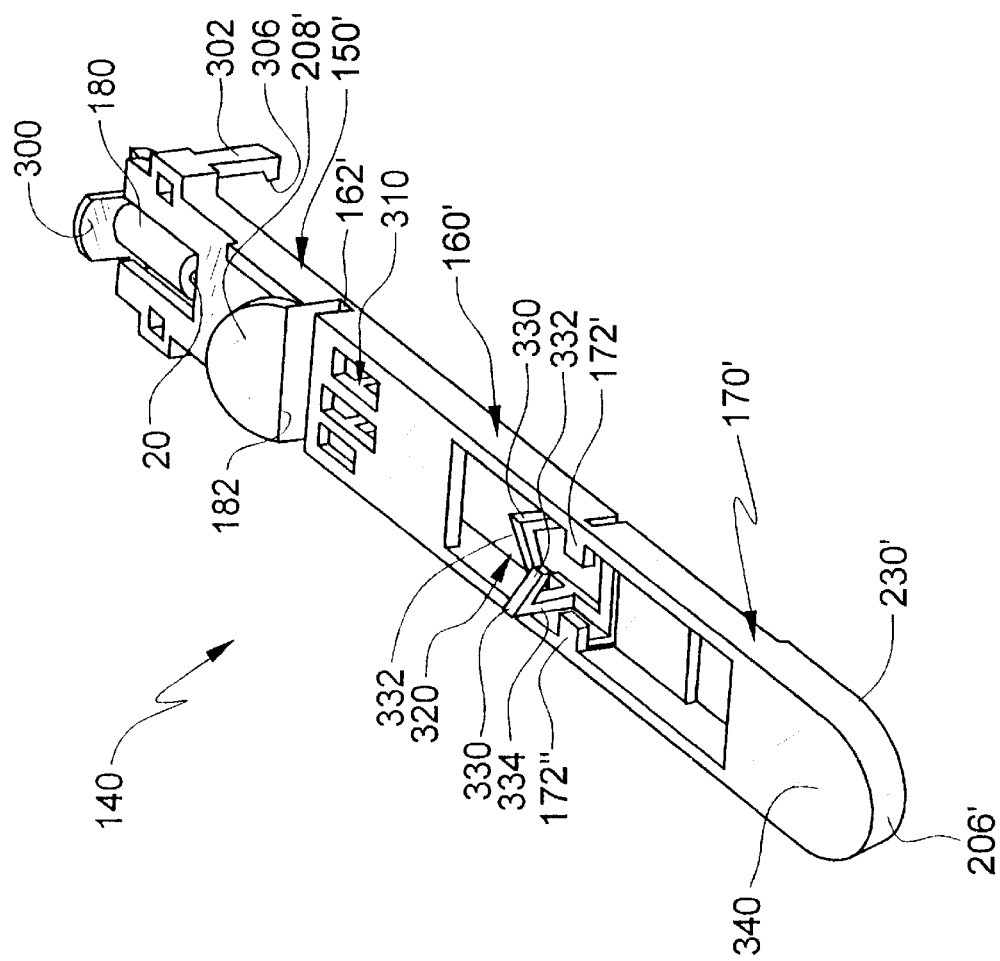
FIG. 12 is an as-molded perspective of another embodiment of the instant invention.
Figure 13:
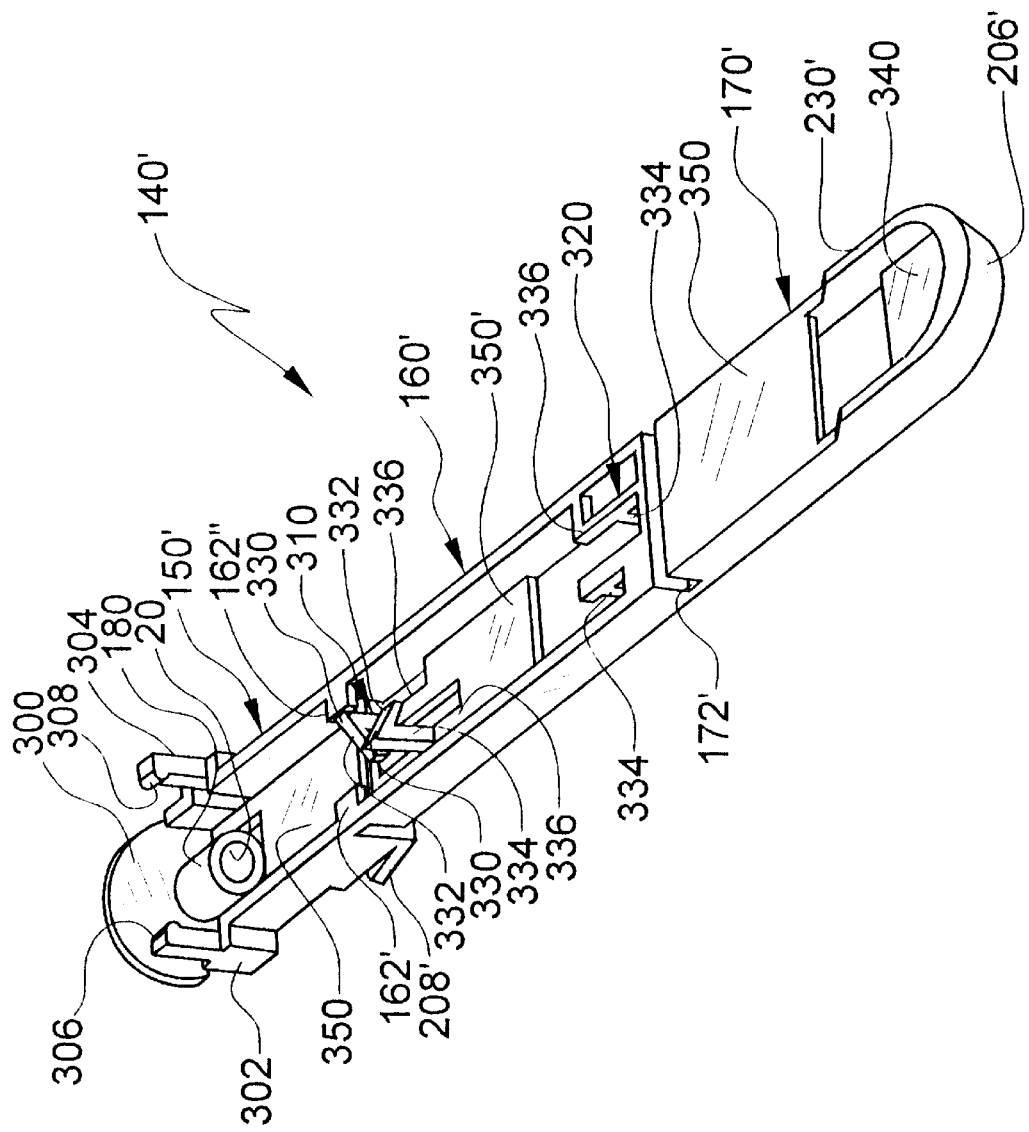
FIG. 13 is a perspective of the embodiment seen in FIG. 14, but rotated so parts hidden in FIG. 12 may be seen.

A presently preferred embodiment of a shroud portion (shroud 140') of the instant invention is provided in FIGS. 12–19. Some parts of this embodiment having substantially the same function as parts numbered above will be identified with primes of numbers used above for clarity of association of previously described function. As-molded parts of shroud 140' are seen in FIGS. 12 and 13. Note that shroud 140' comprises a proximally disposed connecting tab 300. Tab 300 represents a linking member to other parts which are not shown, but which would be molded as part of an integrally molded system. Such other parts may be a phlebotomy barrel, a luer fitting or other connecting part. Shroud 140 of FIGS. 12 and 13 also comprises a needle hub 180, a proximal hinged part 150', a centrally disposed hinged part 160' and a distal hinged part 170'.

Similar to previously disclosed embodiments, parts 150', 160' and 170' are each individually substantially rigid structures. Part 150' is connected to part 160' via hinges 162' and 162". Part 160' is connected to part 170' via hinges 172' and 172".

Part 150' is also hingeably connected to part 300, but the hinges are not shown in FIGS. 12 and 13. Part 150' comprises hub 180, a bulbus or button part 208' disposed at corner 182, and a pair of side clips 302 and 304. Hub 180 comprises an orifice 20' into which a needle 40 is installed and secured to form an assembled needle system which is ready for use in a medical procedure. Each side clip 302 and 304 transversely extends outward from part 150' in a direction which permits contact with part 160' as part 160' is closed upon part 150' as constrained by hinges 162' and 162". Each clip 302 and 304 comprises an inwardly facing protuberance 306 and 308, respectively. Function and purpose of clips 302 and 304 will be disclosed in detail hereafter.

Part 160' comprises a pair of latch sites, 310 and 320. Each latch site comprises an opposing pair of latches, generally numbered 330. Each latch comprises an inwardly protruding and sloping catch member 332 affixed to a riser 334 which is integrally attached to a rail member 336. Generally, each latch 330 functions as previously disclosed for latch 210. However, in the case of each latch 330, spreading is facilitated by lateral displacement of both riser 334 and rail member 336 when a needle 40 is forced toward entrapment in part 160'. It is preferred that engagement of needle 40 by latches 330 be accompanied by a snapping sound to provide an audible indication of a safe state having been achieved as needle 40 is captured in shroud 140'.

Part 170' comprises a needle tip 44 protecting plate 340, a raised section 230' and a closed end 206'. Section 230' provides a raised, physical barrier to protect a user from inadvertent contact with a needle tip 44 after needle 40 is captured in shroud 140'. Each part 150', 160' and 170' comprises at least one structural cross member, generally numbered 350, to assure rigidity of each of the parts. Note that the cross members are disposed to allow clearance for needle 40 as shroud 140' is unfolded.

Figure 15:
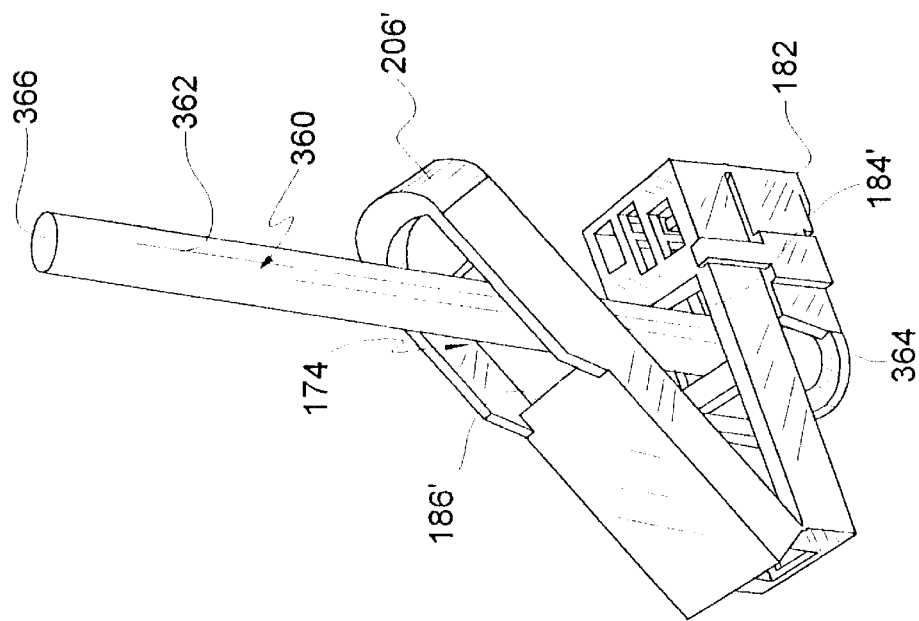
FIG. 15 is a rotated perspective of the sheath assembly of FIG. 14.
Figure 14:
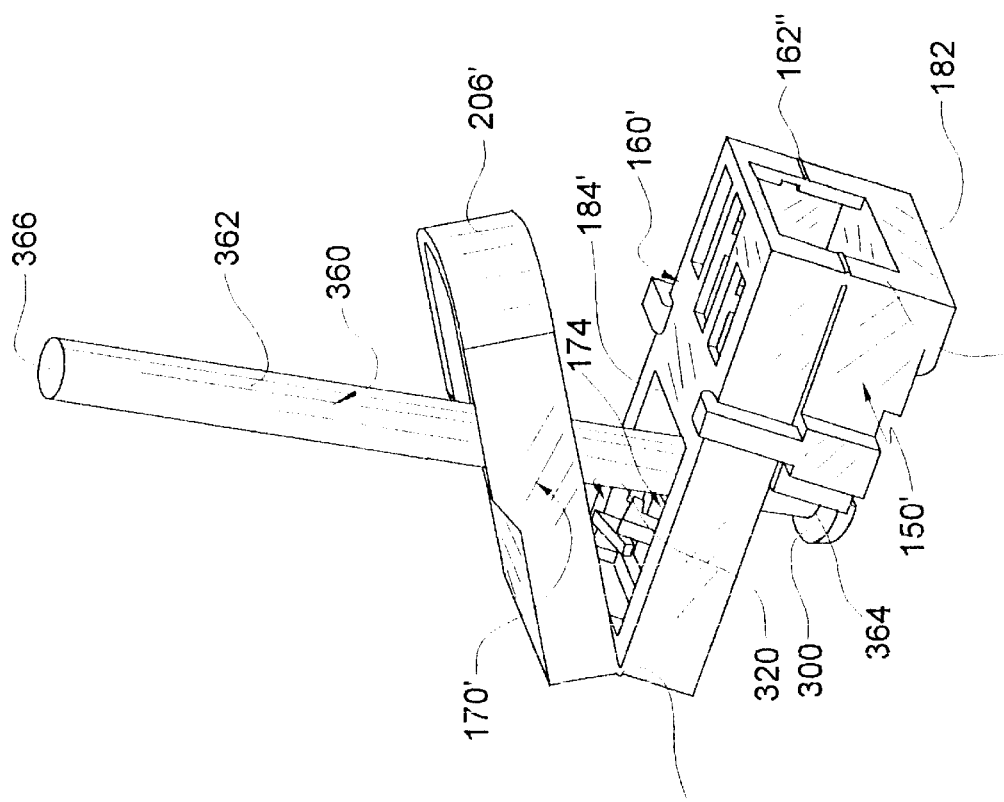
FIG. 14 is a perspective of a sheath assembly comprising a needle cover.
Figure 16:
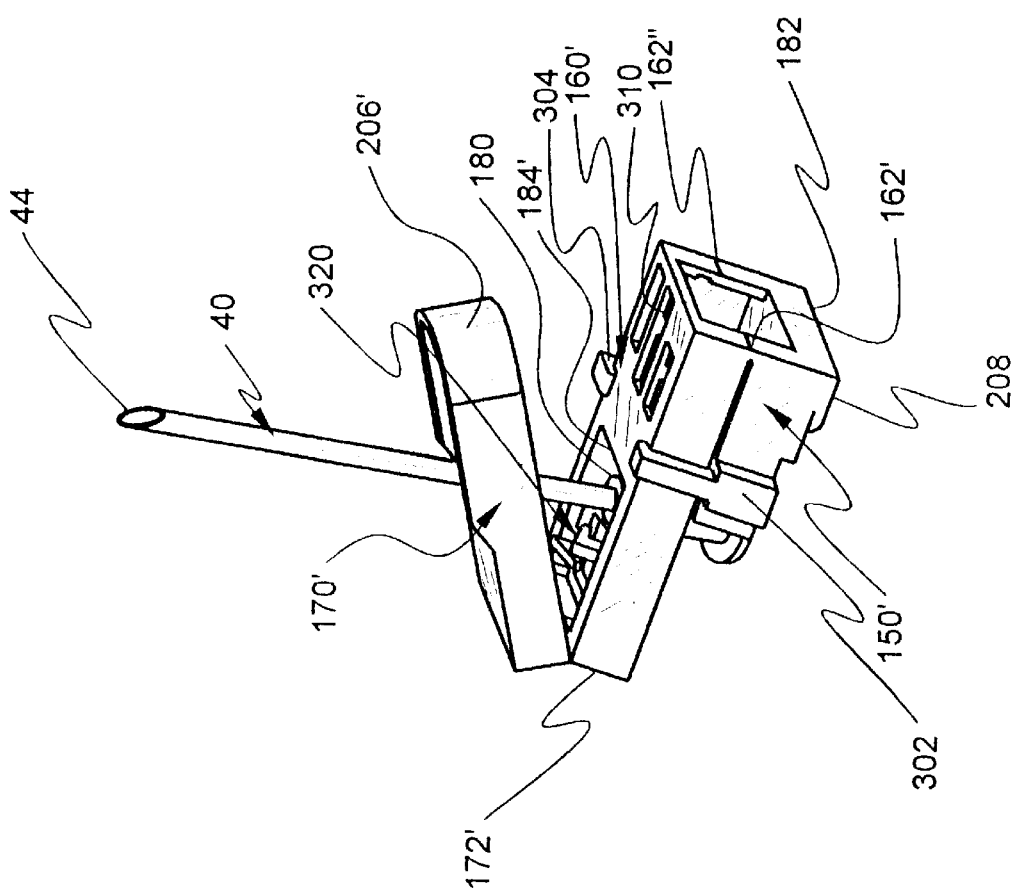
FIG. 16 is a perspective of the sheath assembly of FIG. 14 with needle cover removed.

Reference is now made to FIGS. 14–16. Assembly of a medical-procedure ready device is made by simply securely affixing a needle 40 into hub 130, with parts 150', 160' and 170' folded as seen in FIG. 16. For a more compact fold where part 170' is more parallel with part 160', consideration must be given to assuring that part 170' separates from part 160' when shroud 140' is extended. For that assurance, part 170' must be continuously apart from part 160' at an angle which insures closing angles of intersection between part 170' and needle 40 are always disposed in a non-binding manner. To accomplish this, either an appendage (not shown) may be added to bias parts 160' and 170' apart or an outwardly extending foot or skid, such as foot 189, seen as an example in FIG. 7, may be added to part 170' along line 186' (see FIG. 15 for position of line 186').

A protective cover 360 for needle 40 which is disposed through pathway 174 formed in combination by parts 150', 160' and 170' is seen in FIGS. 14 and 15. Cover 360 comprises an elongated, hollow tubular member 362, an open proximal end 364 and a closed distal end 366. With cover 360 in place, cover 360, shroud 140' and needle 40 and other parts which may be connected to part 300 make up a complete needle 40 protective system. It is important to note that, to make space for insertion of cover 360 along pathway 174 through parts 150', 160' and 170' lines 186' (best seen in FIG. 15) and 184' (best seen in FIG. 14) must be offset from needle 40 to permit passage of cover 360 therethrough.

Cover 360 is removed to bare needle 40 as seen in FIG. 16 before beginning a medical procedure. At the end of the procedure, shroud 140' is extended to engage needle 40 and form a substantially rigid body comprised of needle 40 and shroud 140'. In the extending process, as disclosed previously, rotation of part 150' causes part 160' to rotate which, in turn, causes part 170' to rotate. By their structural geometry, all parts (150', 160', 170') arrive in line (in a single plane) at the same time. However, the offsets mentioned above delay rotation of part 160' relative to part 150' and of part 170' relative to part 160'. As shroud 140' is extended by pressing distally upon corner 182 to rotate part 150', rotation of part 160' is delayed until line 184' comes into contact with needle 40. Subsequently, rotation of part 170' begins when line 186' comes into contact with needle 40. For these reasons, part 170' rotates more rapidly than part 160' about needle 40 at angles of engagement of latches 330 at sites 310 and 320.

Figure 17:
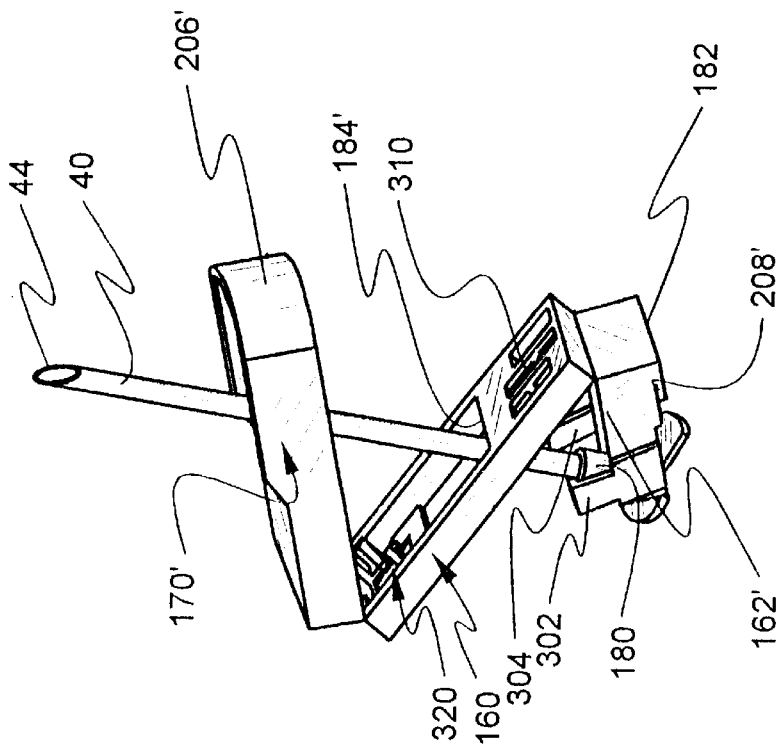
FIG. 17 is a perspective of the sheath assembly of FIG. 16 wherein the sheath is extended toward enclosure of the needle.

An intermediate view of an extending shroud 140' is seen in FIG. 17. Initial rotation of part 150' frees part 160' from releasible containment of clips 302 and 304. Part 160' is displaced by rotation of part 150' until line 184' is in contact with needle 40. Subsequent rotation of part 160' displaces line 186' toward needle 40, but contact between line 186' and needle 40 must occur before part 170' rotates.

Figure 19:
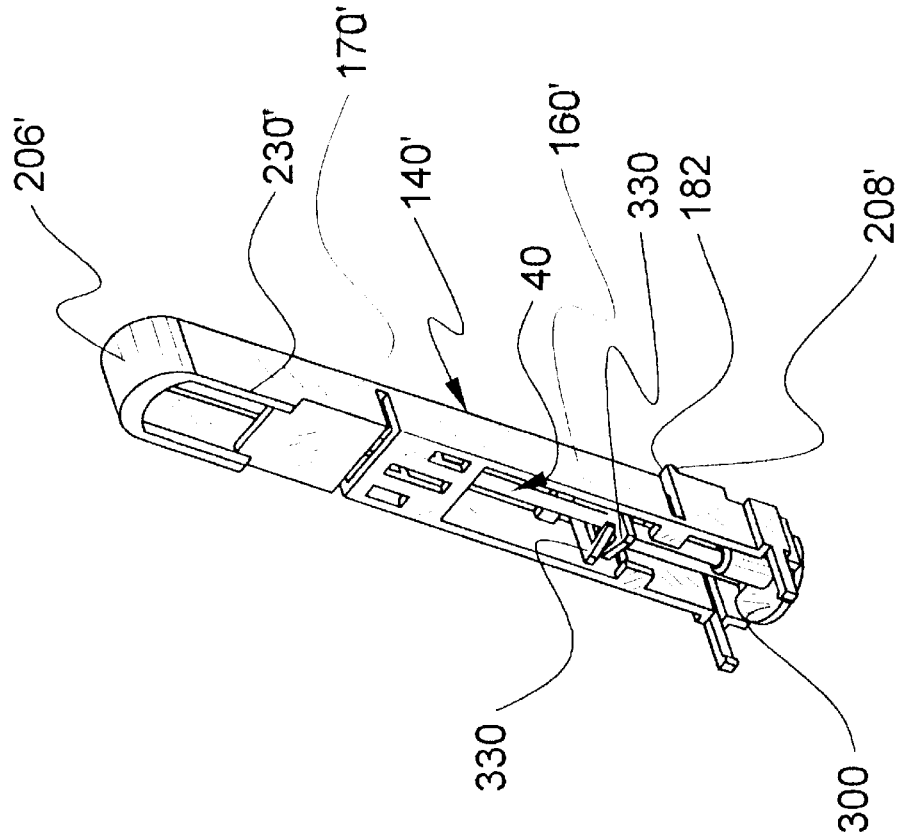
FIG. 19 is a rotated perspective of the sheath assembly of FIG. 18.
Figure 18:
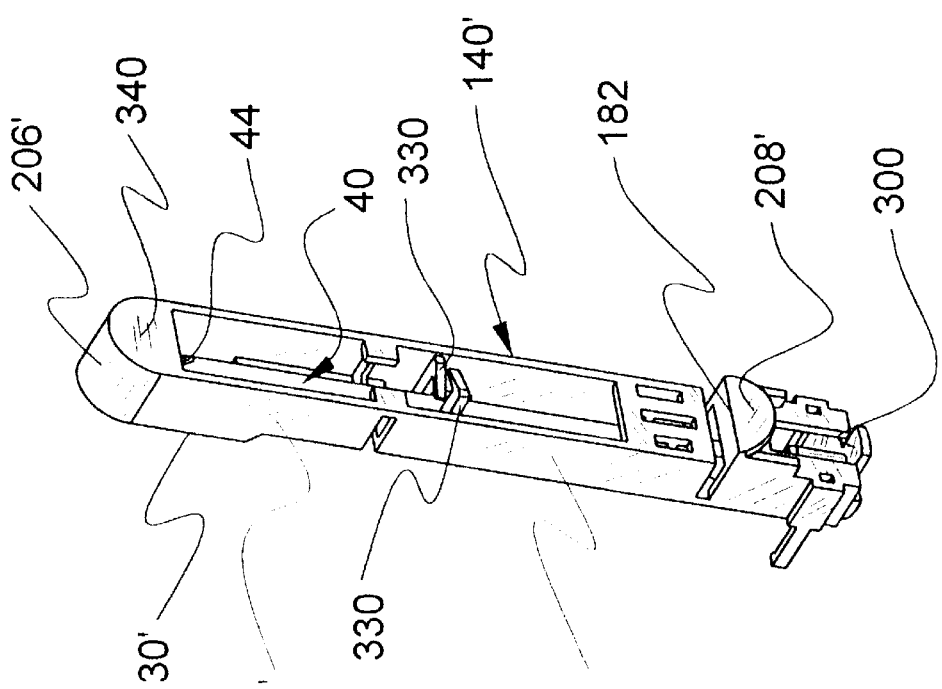
FIG. 18 is a perspective of the sheath assembly of FIG. 16 wherein the sheath is fully extended to a rigid. needle-enclosing state.

FIGS. 18 and 19 provide opposite side perspectives of shroud 140' fully extended to enclose needle 40. Note that all latches 330 are engaged about needle 40. These engagements occur, preferably with an audible snap, as part 160' is rotated into parallel disposition relative to the long axis of needle 40. Movement of any part of shroud 140' is limited by the tightest latch containment and "play" in the hinges, especially hinges 172' and 172". Therefore, it is important to hold tolerances of latches and hinges to reasonably tight limits to assure stability of a shroud 140'/needle 40 combination Access to a shroud 40 protected needle tip 44 is restricted by a combination comprising the substantially fixed length of shroud 140' relative to needle 40, disposition of protecting plate 340 on one side of shroud 140' and height and size of opening in raised section 230' on the other side.

The inventions disclosed herein may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety apparatus for sheathing a medical needle, said apparatus comprising:
    a hollow bore cannula securely affixed in a hub and having at least one sharpened tip to form the medical needle;
    a part hingeably joined to said hub, said part comprising an elongated sheath which comprises a plurality of serially interconnected substantially rigid segments each of which is interconnected to at least one adjacent segment by a hinge, at least a distally disposed segment comprising an open orifice, through which said cannula passes to form a pivotal axis of intersection about the cannula, and a channel in which the cannula is disposed when the sheath is extended, said sheath and said hinges being disposed to permit folding of the sheath about the cannula in a first state to permit usable access to said sharpened tip in a medical procedure and extending of the sheath, while sliding and pivoting the distal segment relative to the cannula, to a substantially planar disposition along said cannula whereat the cannula is disposed along the channel, said sheath further comprising at least one latching member which catches and securely affixes the cannula relative to the sheath, said sheath and cannula, in combination, thereby forming a substantially rigid body which protectively encloses said sharpened tip and denies access thereto.

2. Safety apparatus according to claim 1 wherein a segment which encloses said sharpened tip comprises a closure of its channel distal from the sharpened tip.

3. Safety apparatus according to claim 1 wherein the segment closest to said hub comprises a button which, when disposed toward the cannula extends that segment and the other segments of said sheath along and about said cannula and causes the at least one latching member to be securely affixed relative to the cannula.

4. Safety apparatus according to claim 1 wherein said at least one latching member comprises two latching members.

5. Safety apparatus according to claim 1 wherein a sheath which encloses said sharpened tip comprises an increase in thickness above the channel in the sheath which further protects against contact with the sharpened tip.

6. Safety apparatus according to claim 1 wherein said distally disposed segment comprises a pair of parts disposed on opposite sides of said open orifice which firmly engage opposing sides of said cannula when said sheath is extended, thereby assuring rigidity of the combination of the cannula and extended sheath.

7. A safety apparatus for sheathing a medical needle, said apparatus comprising:
    a hollow bore cannula securely affixed in a hub and having at least one sharpened tip to form the medical needle;
    a part hingeably joined to said hub, said part comprising an elongated sheath which comprises a plurality of serially interconnected substantially rigid segments each of which is interconnected to at least one adjacent segment by an intersegment hinge, at least one segment comprising an open orifice, through which said cannula passes to form a pivotal axis of rotation about the cannula, and a channel along which the cannula is disposed when the sheath is linearly extended, said sheath and said hinges being disposed to permit folding of the sheath about the cannula in a first state to permit usable access to said sharpened tip in a medical procedure and extending of the sheath whereby the at least one sheath pivots about the cannula to a substantially planar disposition along said cannula whereat the needle is disposed within the channel, said sheath further comprising at least one latching member which catches and securely affixes the cannula relative to the sheath, said sheath and cannula, in combination, thereby forming a substantially rigid body which protectively encloses said sharpened tip and denies access thereto.

8. Safety apparatus according to claim 7 wherein a segment which encloses said sharpened tip comprises a closure of its channel distal from the hub and sharpened tip.

9. Safety apparatus according to claim 7 wherein the segment closest to said hub comprises a button which, when depressed to dispose that segment onto said cannula, extends said sheath along and about said cannula and causes the at least one latching member to be securely affixed to the cannula.

10. Safety apparatus according to claim 7 wherein said at least one latching member comprises two latching members.

11. Safety apparatus according to claim 7 wherein the at least one segment comprises a pair of parts disposed on opposite sides of said open orifice which firmly engage opposing sides of said cannula when said sheath is extended, thereby assuring rigidity of the combination cannula and extended sheath.

12. Safety apparatus according to claim 7 wherein said hub and said sheath are, in combination, a single, integral molded part.

13. A method for enclosing a sharpened medical needle in a safety shield comprising the steps of:

providing a hollow bore cannula securely affixed in a hub, said cannula having at least one sharpened tip to form the medical needle, and a part hingeably joined to said hub, said part comprising an elongated sheath which comprises a plurality of serially interconnected substantially rigid segments each of which is interconnected to at least one adjacent segment by an intersegment hinge, at least one segment comprising an open orifice, through which said cannula passes to form a pivotal axis of intersection about the cannula, and a channel in which the cannula is disposed when the sheath is slideably pivoted while being extended to a substantially planar disposition, said sheath and said hinges being disposed to permit folding of the sheath about the cannula in a first state to permit usable access to said sharpened tip in a medical procedure and extending of the sheath to a substantially planar disposition along said cannula whereat the cannula is disposed within the channel, said sheath further comprising at least one latching member which catches to securely affixes the sheath relative to the cannula, said sheath and cannula, in combination, thereby forming a substantially rigid body which protectively encloses said sharpened tip and denies access thereto;

displacing said sheath about said hub and cannula in a compact state such that said needle tip is accessible for a medical procedure;

at the end of the medical procedure, displacing a proximal segment of said sheath to slide and pivot at least one segment about the cannula and thereby unfold segments of the sheath until said at least one latching member is latched relative to said cannula to thereby form the substantially rigid body and protectively enclose and deny access to said at least one sharpened tip.

* * * * *